United States Patent [19]

Landis

[11] Patent Number: 5,691,515
[45] Date of Patent: Nov. 25, 1997

[54] REARWARD SOUND ENHANCING APPARATUS

[75] Inventor: Timothy J. Landis, Loomis, Calif.

[73] Assignee: OP-D-OP, Inc., Roseville, Calif.

[21] Appl. No.: 672,473

[22] Filed: Jun. 28, 1996

Related U.S. Application Data

[63] Continuation-in-part of Ser. No. 586,086, Jan. 16, 1996.

[51] Int. Cl.⁶ .................................................. H04R 25/00
[52] U.S. Cl. ........................... 181/129; 181/130; 381/187
[58] Field of Search .................................... 181/129, 130, 181/135, 137; 381/183, 187, 169, 188; 2/422, 423, 425, 209

[56] References Cited

U.S. PATENT DOCUMENTS

| | | |
|---|---|---|
| 373,835 | 5/1887 | Pitre . |
| 1,528,080 | 3/1925 | Scher .................................. 181/129 |
| 4,471,174 | 9/1984 | Nava .................................... 381/183 |
| 5,044,014 | 9/1991 | Cornale et al. . |
| 5,086,789 | 2/1992 | Tichy . |
| 5,125,032 | 6/1992 | Meister et al. ...................... 381/183 |
| 5,231,704 | 8/1993 | Hildenbrand . |
| 5,361,419 | 11/1994 | Bernstein ............................. 2/209 |
| 5,503,497 | 4/1996 | Landis et al. . |

FOREIGN PATENT DOCUMENTS

| | | |
|---|---|---|
| 912921 | 6/1954 | Germany . |
| 479645 | 4/1953 | Italy . |
| 356552 | 9/1931 | United Kingdom . |

*Primary Examiner*—Khanh Dang
*Attorney, Agent, or Firm*—John P. O'Banion

[57] ABSTRACT

A rearward sound enhancing apparatus which includes a pair of ear covers mounted on a headband. Each ear cover includes an inner compartment and outer compartment with rearward facing openings. A microphone is provided in each outer compartment, and a speaker is provided in each inner compartment. Sound received through the rearward facing opening is picked up by the microphones, amplified, and directed to the speakers. The dual compartment arrangement of the ear covers eliminates audio feedback which would otherwise occur due to the close proximity of microphones and speakers in the ear covers.

18 Claims, 2 Drawing Sheets

REARWARD SOUND ENHANCING APPARATUS

CROSS REFERENCE TO RELATED APPLICATIONS

This application is a continuation-in-part of copending application Ser. No. 08/586,086, filed Jan. 16, 1996.

BACKGROUND OF THE INVENTION

1. Field of the Invention

This invention pertains generally to devices and methods for directional receiving and amplification of sound, and more particularly to a head-worn, rearward sound enhancing apparatus for use by cyclists and the like which amplifies sounds from behind the wearer and directs the amplified sounds to the wearer's ears.

2. Description of the Background Art

Bicycle travel has grown in popularity in recent years, and the number of bicycles and bicyclists has proliferated as people have generally become more health and environmentally conscious. One problem associated with bicycle travel is that the hearing of cyclists, especially in the rearward direction, is reduced by the noise caused by air or wind rushing past the ears due to the speed of travel. The reduced hearing associated with bicycle travel increases the risk of collisions with motor vehicles or other bicycles, particularly those approaching from the rear, because cyclists may not hear an approaching vehicle which they could otherwise react to in order to avoid a collision.

A variety of ear covering, ear protector, and wind-deflector devices have been developed to both protect the ears of cyclists and to reduce the wind noise associated with bicycle travel. Most of these devices comprise shell-like coverings which are held over the ears of a wearer by a resilient band or head encircling strap. Some of the known ear covering devices include rearwardly disposed openings which provide for passive sound amplification or collection from the rear. However, previously disclosed ear covering and ear protecting devices have generally failed to provide adequate active rearward sound amplification which overcomes the wind noise associated with cycle travel sufficiently to allow cyclists to hear motor vehicles or other cyclists approaching from the rear.

Accordingly, there is a need for an apparatus which provides for the receiving and amplification of sounds from behind a wearer, which directs the amplified sound to a wearer's ears, which overcomes the wind noise associated with bicycle travel, and which increases the safety of bicycle travel. The present invention satisfies these needs, as well as others, and generally overcomes the deficiencies found in conventional devices.

SUMMARY OF THE INVENTION

The present invention pertains to a head-worn, rearward-facing, acoustic receiver apparatus for enhancing the hearing of cyclists in the rearward direction. In general terms, the invention comprises a pair of head-worn ear covers, each of which includes a pair of compartments which open towards the rear. The pair of compartments comprise an outer compartment and an inner compartment separated by a wall or barrier, with the inner compartment of each ear cover positioned adjacent one of the wearer's ears. The inner and outer compartments each include a rearward facing opening through which sound is received. A microphone is included in each of the outer compartments, and an earphone or speaker is provided in each of the inner compartments. An amplifier and battery power supply are also preferably included in each outer compartment. Means for attaching the ear covers to a wearer's head are provided with the invention.

By way of example and not of limitation, the ear covers are aerodynamically shaped to minimize wind drag and the wind noise generally associated with bicycle travel. The outer compartment of each ear cover generally defines an acoustic receiver which is structured and configured to receive sound waves from the rearward facing opening and direct or reflect the sound waves to the microphone contained therein. Each microphone is optimally positioned within its respective outer compartment for picking up sound received by the outer compartment. Sound received by the microphones is amplified and directed to the earphones located in the inner compartments of each ear cover. The inner compartments also serve as acoustic receivers and passively amplify sound received from the rearward facing openings and direct the amplified sound to the wearer's ears. The earphones in the inner compartments preferably comprise conventional small audio speakers which are interfaced with the microphones, amplifiers and power supply by standard wiring. The head attachment or support means preferably comprises a conventional headband which is preferably structured and configured to be worn in association with a cycling helmet or other head protective gear. Means for positionally adjusting the ear covers relative to the wearer's ears are preferably included with the head attachment means in the form of articulating hinges or links associated with the headband adjacent to each ear cover.

The invention is utilized by fastening the headband to the wearer's head in a conventional manner, with the ear covers positioned over the wearer's ears, with the inner compartment of each ear cover positioned adjacent the wearer's ears, and with the openings in the inner and outer compartments facing towards the rear. The articulating hinges are adjusted to optimally position the ear covers for wearer comfort. Sound received through the rearward openings of the outer compartments is reflected to the microphones contained therein, and thence amplified and directed to the earphones within the inner compartments adjacent the wearer's ears. The rearward facing openings of the inner compartments additionally provide passive sound amplification to the wearer of sounds from the rear. Wind-generated noise, which traditionally limits the hearing of cyclists, is reduced or eliminated by the ear covers, allowing the amplified sound from the rear to reach the wearer's ears. The invention thus allows the wearer to hear the sounds of traffic approaching from behind which would otherwise not be audible to the wearer.

The use of dual compartment ear covers with the microphones and speakers located in separate compartments of each ear cover reduces or eliminates undesirable audio feedback which would otherwise occur due to the close proximity of the microphone, speaker and amplifier present in each ear cover. The removal of such audio feedback further enhances the sound provided to the wearer.

An object of the invention is to provide a rearward sound enhancing apparatus which allows cyclists to hear the sounds of approaching traffic from behind.

Another object of the invention is to provide a rearward sound enhancing apparatus which eliminates the wind noise associated with bicycle travel.

Another object of the invention is to provide a rearward sound enhancing apparatus which may be interchangeably used with different cycling helmets.

Another object of the invention is to provide a rearward sound enhancing apparatus which is inexpensive to manufacture.

Another object of the invention is to provide a rearward sound enhancing apparatus which is easy to use.

Another object of the invention is to provide a rearward sound enhancing apparatus which increases or enhances the safety of bicycle travel and reduces the risk of collision or accidents.

Another object of the invention is to provide a rearward sound enhancing apparatus which reduces or eliminates undesirable audio feedback Further objects of the invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
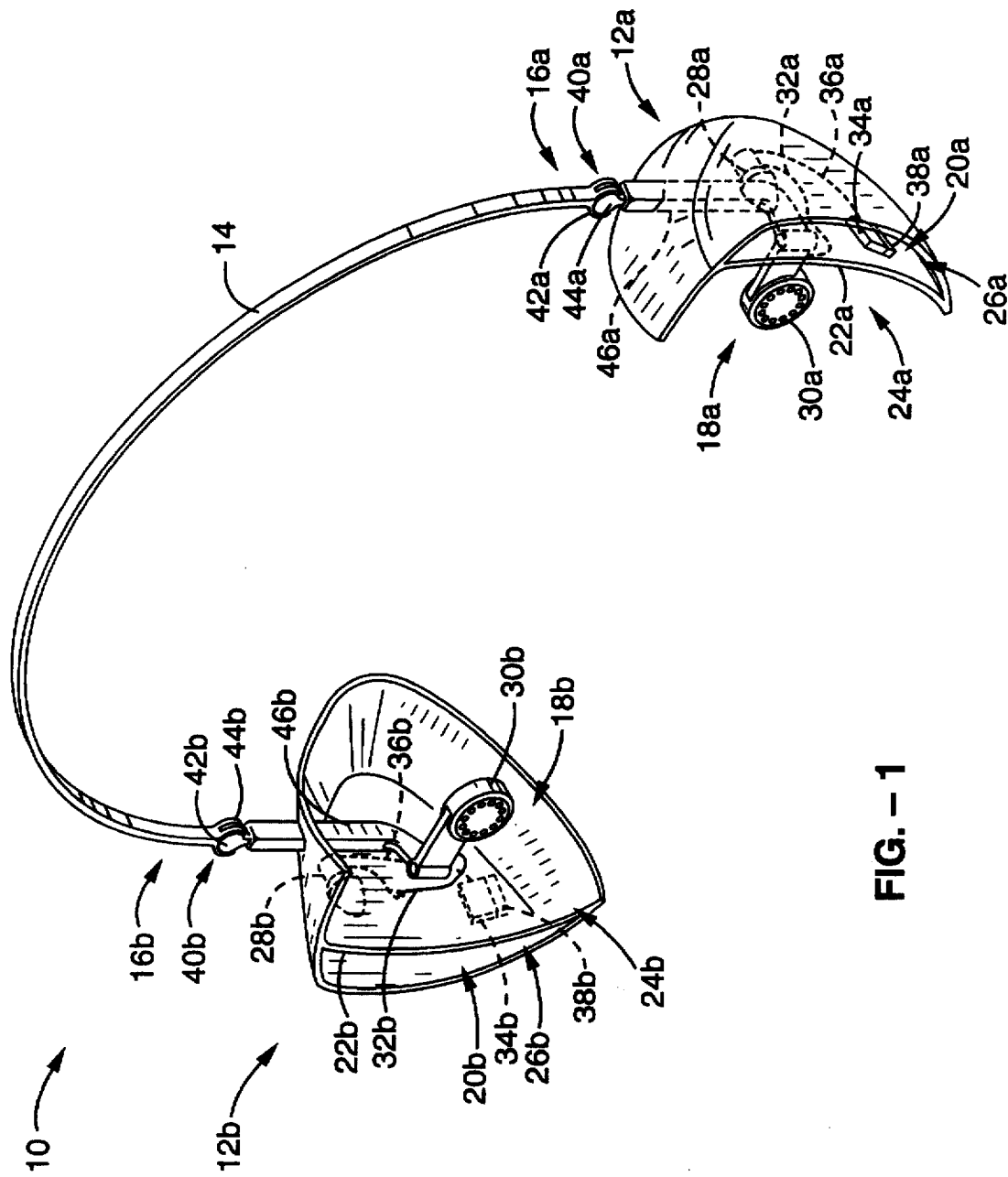
FIG. 1 is a perspective view of an apparatus in accordance with the present invention.
Figure 2:
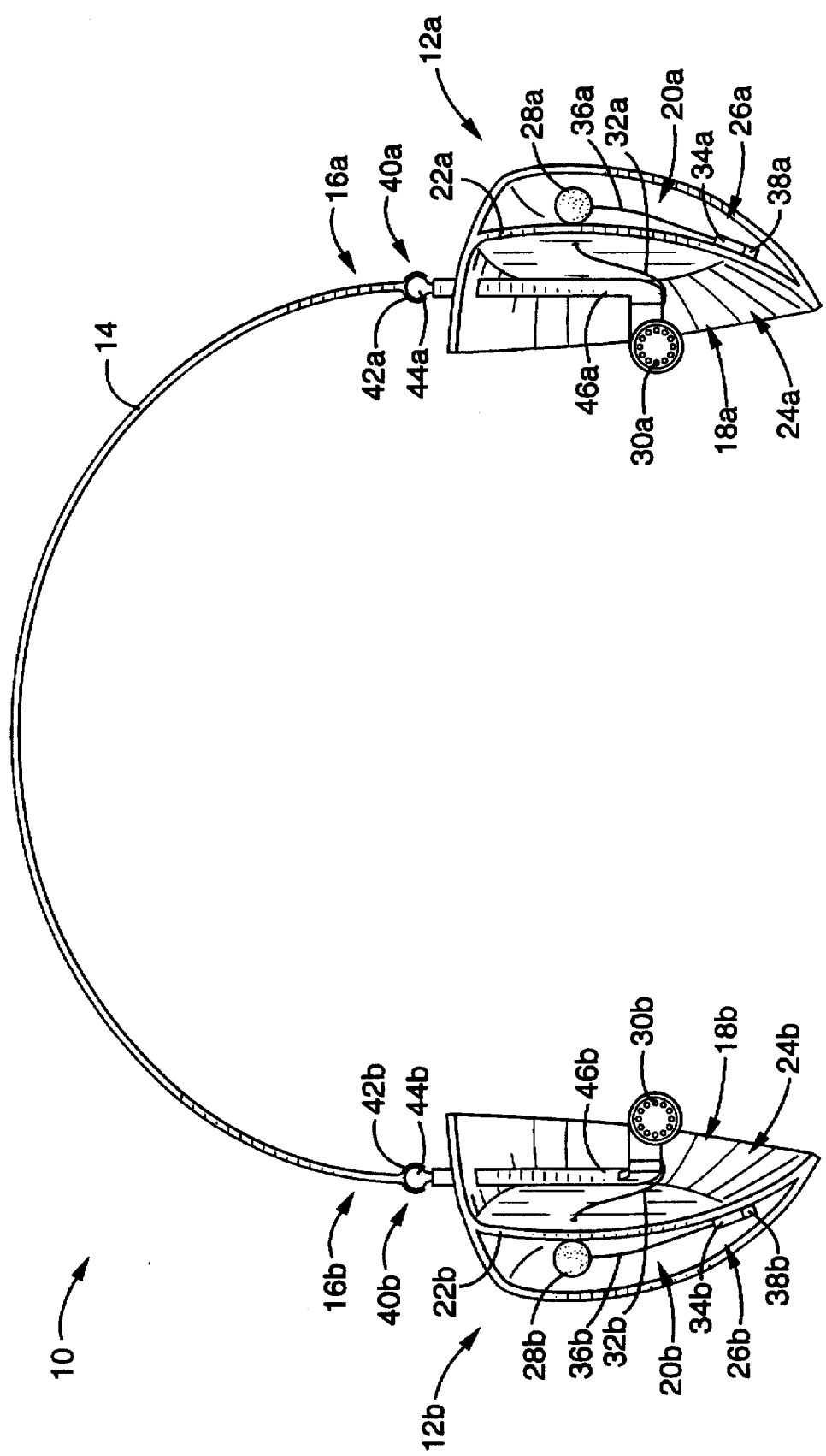
FIG. 2 is a rear view of the apparatus shown in FIG. 1.

Referring more specifically to the drawings, for illustrative purposes the present invention is embodied in the apparatus which is generally shown in FIG. 1 and FIG. 2. It will be appreciated that the apparatus may vary as to configuration and as to details without departing from the basic concepts as disclosed herein. While the invention is described herein in terms of use by bicyclists, it should be readily apparent that the invention may also be used by motorcyclists and by persons engaged in other non-cycling activities such as jogging wherein reception and amplification of sound from behind or outside the wearer's line of sight is desirable.

Referring now to FIG. 1 and FIG. 2, a rearward hearing enhancement apparatus 10 is generally shown. The apparatus 10 includes first and second ear covers 12a, 12b which are coupled to a resilient headband 14 at first and second ends 16a, 16b thereof, respectively. Ear covers 12a, 12b are aerodynamically shaped to minimize wind drag and the wind noise generally associated with bicycle travel. First ear cover 12a comprises a first inner compartment 18a and a first outer compartment 20a which are separated from each other by a barrier or wall 22a. Second ear cover 12b likewise comprises a second inner compartment 18b and second outer compartment 20b which are separated from each other by a barrier or wall 22b. First inner compartment 18a has a rearward facing opening 24a, and first outer compartment 20a has a rearward facing opening 26a. Second inner compartment 18b and second outer compartment 20b of second ear cover 12b likewise include rearward facing openings 24b, 26b, respectively.

Outer compartments 20a, 20b each generally define an acoustic receiver and are structured and configured to receive sound through rearward facing openings 26a, 26b, respectively, and to reflect or focus the sound received into the interiors of outer compartments 20a, 20b. A pair of microphones 28a, 28b are provided with the invention, and are located inside first and second outer compartments 20a, 20b, respectively. Microphones 28a, 28b are optimally positioned within outer compartments 20a, 20b, respectively, to receive or pick up reflected sound obtained through rearward facing openings 26a, 26b.

A pair of speakers or earphones 30a, 30b are also included with the invention, and are located within first and second inner compartments 18a, 18b, respectively. Speakers 30a, 30b are operatively coupled to or interfaced with microphones 28a, 28b, respectively, via wiring 32a, 32b. Speakers 30a, 30b are positioned within inner compartments 18a, 18b such that speakers 30a, 30bare adjacent to the wearer's ears when ear covers 12a, 12b are placed over the wearer's ears. Sound received by microphones 28a, 28b is directed to speakers 30a, 30b via wiring 32a, 32b in a conventional manner. Inner compartments 18a, 18b are also structured and configured to serve as acoustic receivers, and sound received through rearward facing openings 24a, 24b of inner compartments 18a, 18b is passively amplified by the shape of inner compartments 18a, 18b and directed towards the ears of the wearer.

Means for amplifying sound received by microphones 28a, 28b are preferably included with the invention, and are shown generally as amplifiers 34a, 34b located within outer compartments 20a, 20b, respectively, of ear covers 12a, 12b. Amplifiers 34a, 34b are interfaced with microphones 28a, 28b and speakers 30a, 30b via wiring 36a, 36b, respectively. Preferably, power supply means in the form of batteries 38a, 38b are also included with the invention and are positioned adjacent amplifiers 34a, 34b, respectively, in outer compartments 20a, 20b. The power supply means may alternatively comprise a solar cell array or arrays (not shown) which are associated with the upper surfaces of ear covers 12a, 12b and/or headband 14. Amplifier 34a and battery 38a may be integral to a circuit board (not shown) mounted on wall 22a within outer compartment 20a, with amplifier 34b, and battery 38b likewise associated with a circuit board (not shown) and mounted on wall 22b within outer compartment 20b. A volume control (not shown) may also be included with the invention, particularly if amplifiers 34a, 34b are used, to allow the user of the invention to increase or decrease the power output of earphones 30a, 30b as required. If desired, an FM radio, intercom system, or like audio system may be included with the invention in association with amplifiers 34a, 34b to allow users of the invention to listen to radio broadcasts or to receive communication from others via speakers 30a, 30b.

As related above, first and second ear covers 12a, 12b are coupled respectively to first and second ends 16a, 16b of headband 14, which serves as means for supporting ear covers 12a, 12b on a wearer's head. Other support means may be used in conjunction with ear covers 12a, 12b if desired. For example, a head-encircling strap may be used to support ear covers 12a, 12b on the wearer's head, or ear covers 12a, 12b may be supported directly by a hat, visor, bicycle helmet, eye-glass frame or other head-worn item. Headband 14 is preferably structured and configured to be worn with a conventional cycling helmet or other protective head gear.

Preferably, means for positionally adjusting ear covers 12a, 12b relative to the wearer's ears are included with the invention. The positional adjusting means is shown in FIG. 1 and FIG. 2 as a pair of articulating hinges or links 40a, 40b positioned generally between first and second ends 16a, 16b respectively of headband 14 and ear covers 12a, 12b. Hinges 40a, 40b each include a generally "C"-shaped socket 42a, 42b of resilient construction and which are joined to first and second ends 16a, 16b respectively of headband 14. Hinges 40a, 40b also each include a generally cylindrical tongue or post 44a, 44b which snap fit into sockets 42a, 42b respectively in a pivotal relationship. Posts 44a, 44b are joined respectively to connecting members 46a, 46b which in turn are attached to ear covers 12a, 12b respectively, with connecting members generally acting as articulating extensions of headband 14. Speakers 30a, 30b are mounted on connecting members 46a, 46b. By applying a force to ear covers 12a, 12b, posts 44a, 44b are caused to pivot or rotate relative to sockets 42a, 42b, allowing ear covers 12a, 12b (and connecting members 46a, 46b) to be positionally adjusted relative to headband 14 and the wearer's head. The adjusted positions for ear covers 12a, 12b are retained by hinges 40a, 40b once the force is removed from ear covers 12a, 12b. If desired, a plurality of inter-engaging teeth or serrations (not shown) may be included on the inner surfaces of sockets 44a, 44b and the outer surfaces of posts 46a, 46b so that hinges 40a, 40b articulate in a ratcheting fashion. A similar hinge arrangement suitable for use as the positional adjustment means of the present invention is described in U.S. Pat. No. 5,503,497 issued on Apr. 2, 1996 owned by the assignee hereof, the disclosure of which is incorporated herein by reference. Alternatively, ball and socket hinges, pintle and gudgeon hinge arrangements, and bendable portions of headband 14 may be used to positionally adjust ear covers 12a, 12b relative to headband 14 and the wearer's head. Further, ear covers 12a, 12b could be coupled directly to a bicycle helmet in the same manner. Other positional adjustment means will suggest themselves to those of ordinary skill in the art, and are also considered to be within the scope of this disclosure.

The rearward sound enhancement apparatus 10 is utilized by fitting headband 14 on a wearer's head in a conventional manner, and placing ear covers 12a, 12b over the wearer's ears such that the wearer's ears fit within inner compartments 18a, 18b of ear covers 12a, 12b, speakers 30a, 30b are positioned adjacent the wearer's ears. A cyclist helmet or hat may be worn over headband 14 if desired. The openings 24a, 24b in inner compartments 18a, 18b, and openings 26a, 26b in outer compartments 20a, 20b are oriented towards the wearer's rear or in a rearward-facing direction. Ear covers 12a, 12b and speakers 30a, 30b may be optimally positioned by use of articulating hinges 40a, 40b as described above. While the invention is thus worn, sounds from behind the wearer, such as the sounds of an approaching vehicle, are received through rearward facing openings 26a, 26b of outer compartments 20a, 20b and reflected or directed to microphones 28a, 28b which are respectively contained therein. The sound thus picked up by microphones 28a, 28b is amplified by amplifiers 34a, 34b and directed to speakers 30a, 30b in a conventional manner. At the same time, sound from behind the wearer is received through rearward facing openings 24a, 24b of inner compartments 18a, 18b and is passively amplified by inner compartments 18a, 18b and provided to the wearer's ears to supplement the sound provided to the wearer by speakers 30a, 30b. Ear coverings 12a, 12b eliminate the ambient wind noise associated with cycle travel, so that the sounds produced by earphones 34a, 34b may be heard clearly by the user of the invention.

The close proximity of microphone 28a, speaker 30a and amplifier 34a within ear cover 12a, and microphone 28b, speaker 30b and amplifier 34b in ear cover 12b creates the possibility of undesirable audio feedback which would detract from the rearward sound enhancement provided by the invention. The dual compartment arrangement of ear covers 12a, 12b, however, places the microphones and amplifiers in separate compartments from the speakers, and serves to reduce or eliminate audio feedback which would otherwise be associated with the electronic amplification of sound received by microphones 28a, 28b and directed to speakers 30a, 30b.

Ear covers 12a, 12b are preferably made of a durable polymeric substance such as an engineering resin, or a reinforced composite material thereof. Walls 22a, 22b which define the inner and outer compartments within ear covers 12a, 12b are preferably integral to ear covers 12a, 12b and made of the same material. Headband 14 is preferably of conventional resilient metal and/or polymeric construction and may be extensible to accommodate varying head sizes, as is standard in the art. The size and shape of ear covers 12a, 12b and inner and outer compartments 18a, 18b, 20a, and 20b may be varied as required for different applications of the invention. Thermal insulation and/or acoustic insulation may be included with ear covers 12a, 12b if desired. Rearward facing openings 24a, 24b of inner compartments 18a, 18b additionally provide ventilation to the wearer's ears as well as passive sound amplification.

Use of the invention increases the safety of bicycle travel by allowing the wearer of the invention to hear sounds associated with vehicles approaching from behind which are not visible to the cyclist and would otherwise not be heard by the cyclist due to the ambient wind noise in the ears of the cyclist which is inherent in bicycle travel. The wearer of the invention, upon hearing a vehicle approaching from behind, may take responsive action, such as directing the bicycle towards the shoulder of the roadway, in order to avoid a collision. The invention may be utilized by cyclists in bicycle racing applications, as the invention allows the user to hear or detect the approach of other cyclists from behind without expending the effort of turning the head to look for other cyclists.

While the invention is described herein in terms of use by bicyclists, it should be readily apparent that the invention may also be used by motorcyclists and by persons engaged in other non-cycling activities such as jogging wherein reception and amplification of sound from behind or outside the wearer's line of sight is desirable. Additionally, while the invention is described in terms of utilizing rearward facing openings 24a, 24b, 26a, 26b, sound enhancement may be obtained in other directions with the invention by suitably orienting the position of the openings 24a, 24b, 26a, 26b of the inner and outer compartments 18a, 18b, 20a, 20b of ear covers 12a, 12b. Further, it will be appreciated that a single ear cover/microphone/speaker assembly could be employed instead of a pair.

Accordingly, it will be seen that the present invention provides a rearward sound enhancing apparatus which reduces or eliminates ambient wind noise due to air rushing past the cyclist's ears, which receives sound from the rear direction and provides the sound to the wearer of the invention, and which reduces or eliminates audio feedback associated with amplification of received sound. Although the description above contains many specificities, these should not be construed as limiting the scope of the invention but as merely providing illustrations of some of the presently preferred embodiments of this invention. Thus, the scope of the invention should be determined by the appended claims and their legal equivalents.

What is claimed is:

1. A rearward sound enhancing apparatus worn over a wearer's ear, comprising:

(a) an ear cover, said ear cover including an inner compartment and an outer compartment, said inner and outer compartments each having a rearward facing opening;

(b) a microphone, said microphone mounted within said outer compartment of said ear cover;

(c) a speaker, said speaker mounted within said inner compartment of said ear cover, said speaker electrically connected to said microphone; and (d) support means, coupled to said ear cover, for supporting said ear cover over a wearer's ear.

2. An apparatus as recited in claim 1, wherein said support means includes means for adjusting the position of said ear cover relative to said wearer's ear.

3. An apparatus as recited in claim 1, wherein said support means comprises a resilient headband, said headband including first and second ends, said ear cover coupled to one said end of said headband.

4. An apparatus as recited in claim 1, further comprising means for supplying power to said microphone and said speaker.

5. An apparatus as recited in claim 1, wherein said inner and outer compartments are separated by a wall.

6. An apparatus as claimed in claim 1, further comprising means, electrically connected between said microphone and said speaker, for amplifying sound received by said microphone.

7. A rearward sound enhancing apparatus worn over a wearer's ear, comprising:

(a) a first ear cover, said first ear cover including a first inner compartment and a first outer compartment, said first inner compartment and said first outer compartment each having a rearward facing opening;

(b) a second ear cover, said second ear cover including a second inner compartment and a second outer compartment, said second inner compartment and said second outer compartment each having a rearward facing opening;

(c) first and second microphones, said first microphone mounted within said first outer compartment, said second microphone mounted within said second outer compartment; and (d) first and second speakers, said first speaker mounted within said first inner compartment, said second speaker mounted within said second inner compartment, said first speaker electrically connected to said first microphone, said second speaker electrically connected to said second microphone; and (e) support means, coupled to said first and second ear covers, for supporting said first and second ear covers on a wearer's head and over said wearer's ears.

8. An apparatus as recited in claim 7, wherein said support means includes means for adjusting the position of said first and second ear covers relative to said wearer's ears.

9. An apparatus as recited in claim 7, wherein said support means comprises a resilient headband, said headband including first and second ends, said first ear cover coupled to said first end of said headband, said second ear cover coupled to said second end of said headband.

10. An apparatus as recited in claim 7, further comprising means for supplying power to said first and second microphones and said first and second speakers.

11. An apparatus as recited in claim 7, wherein said first inner compartment and said first outer compartment are separated by a wall, and said second inner compartment and said second outer compartment are separated by a wall.

12. An apparatus as recited in claim 7, further comprising first and second amplifiers, said first amplifier mounted within said first outer compartment and electrically connected between said first microphone and said first speaker, said second amplifier mounted within said second outer compartment and electrically connected between said second microphone and said second speaker.

13. An apparatus as recited in claim 8, wherein said adjusting means comprises first and second articulating hinges, said first articulating hinge positioned between said first ear cover and said supporting means, said second articulating hinge positioned between said second ear cover and said supporting means.

14. A rearward sound enhancing apparatus worn over a wearer's ear, comprising:

(a) a first ear cover, said first ear cover including a first inner compartment and a first outer compartment, said first inner compartment and said first outer compartment each having a rearward facing opening, said first inner compartment and said first outer compartment separated by a first wall;

(b) a second ear cover, said second ear cover including a second inner compartment and a second outer compartment, said second inner compartment and said second outer compartment each having a rearward facing opening, said second inner compartment and said second outer compartment separated by a second wall;

(c) first and second microphones, said first microphone mounted, within said first outer compartment, said second microphone mounted within said second outer compartment;

(d) first and second speakers, said first speaker mounted within said first inner compartment, said second speaker mounted within said second inner compartment, said first speaker electrically connected to said first microphone, said second speaker electrically connected to said second microphone; and (e) first and second amplifiers, said first amplifier mounted within said first outer compartment and electrically connected between said first microphone and said first speaker, said second amplifier mounted within said second outer compartment and electrically connected between said second microphone and said second speaker; and (f) support means, coupled to said first and second ear covers, for supporting said first and second ear covers on a wearer's head and over said wearer's ears.

15. An apparatus as recited in claim 14, wherein said support means includes means for adjusting the position of said first and second ear covers relative to said wearer's ears.

16. An apparatus as recited in claim 14, wherein said support means comprises a resilient headband, said headband including first and second ends, each said ear cover coupled to one said end of said headband.

17. An apparatus as recited in claim 14, further comprising means for supplying power to said first and second microphones, said first and second speakers and said first and second amplifiers.

18. An apparatus as recited in claim 16, wherein said adjusting means comprises first and second articulating hinges, said first articulating hinge positioned on said first end of said resilient headband adjacent said first ear cover, said second articulating hinge positioned on said second end of said resilient headband adjacent said second ear cover.

* * * * *